US007385096B2

(12) United States Patent
Tanaka et al.

(10) Patent No.: US 7,385,096 B2
(45) Date of Patent: Jun. 10, 2008

(54) PROCESS FOR PRODUCING 1,2-DIOL

(75) Inventors: Masato Tanaka, Ibaraki (JP); Kazuhiko Sato, Ibaraki (JP); Yoko Usui, Chiba (JP)

(73) Assignees: Japan Science and Technology Agency, Saitama (JP); National Institute of Advanced Industrial Science and Technology, Tokyo (JP)

( * ) Notice: Subject to any disclaimer, the term of this patent is extended or adjusted under 35 U.S.C. 154(b) by 511 days.

(21) Appl. No.: 10/500,560

(22) PCT Filed: Jan. 23, 2003

(86) PCT No.: PCT/JP03/00593

§ 371 (c)(1),
(2), (4) Date: Jun. 30, 2004

(87) PCT Pub. No.: WO03/062179

PCT Pub. Date: Jul. 31, 2003

(65) Prior Publication Data
US 2005/0096480 A1 May 5, 2005

(30) Foreign Application Priority Data
Jan. 24, 2002 (JP) ............................. 2002-015146

(51) Int. Cl.
C07C 5/00 (2006.01)
(52) U.S. Cl. ..................................... 585/250
(58) Field of Classification Search ................ 585/250
See application file for complete search history.

(56) References Cited

U.S. PATENT DOCUMENTS

| 2,813,908 | A | 11/1957 | Young et al. |
| 4,286,068 | A | 8/1981 | Mares et al. |
| 5,414,153 | A | 5/1995 | Costantini |

FOREIGN PATENT DOCUMENTS

| EP | 132783 A1 | 2/1985 |
| EP | 0 146 374 A2 | 6/1985 |
| GB | 1020051 A | 2/1966 |
| GB | 1 208 144 A | 10/1970 |
| JP | 4-41449 A | 2/1992 |
| JP | 10-45644 A | 2/1998 |

OTHER PUBLICATIONS

English Translation of the International Preliminary Examination Report.
Schwegler et al., "Heteropolyanions As Oxidation Catalysts in a 2-Phase System," Tetrahedron Letters, vol. 29, No. 7, pp. 823-826, Pergamon Journals Ltd. (1988).
Venturello, "A Convenient Catalytic Method for the Dihydroxylation of Alkenes by Hydrogen Peroxide," Synthesis, pp. 295-297 (Apr. 1989).
Corma et al., "Activity of Ti-Beta Catalyst for the Selective Oxidation of Alkenes and Alkanes," Journal of Catalysis, vol. 145, pp. 151-158, Academic Press, Inc. (1994).
Tatsumi et al., "Remarkable activity enhancement by trimethylsilylation in oxidation of alkenes and alkanes with $H_2O_2$ catalyzed by titanium-containing mesoporous molecular sieves," Chem. Communications, pp. 325-326, (1998).
Fraile et al., "Silica-Supported Titanium Derivatives as Catalysts for the Epoxidation of Alkenes with Hydrogen Peroxide: A New Way to Tuneable Catalytic Activity through Ligand Exchange," Journal of Catalysis, vol. 189, pp. 40-51, Academic Press (2000).
Swern et al., "Hydroxylation of Monounsaturated Fatty Materials with Hydrogen Peroxide," Journal of the American Chemical Society, vol. 67, pp. 1786-1789 (1945).
Mugdan et al., "Catalytic Hydroxylation of Unsaturated Compounds," Journal of Chemical Society, pp. 2988-2999 (1949).
Luong et al., "Direct Hydroxylation of Fats and Derivatives with a Hydrogen Peroxide Tungstic Acid System," Journal of American Oil Chemical Society, vol. 44, pp. 316-320, (May 1967).
Roebuck et al., "*trans*-1,2-Cyclohexanediol," Organic Syntheses Collective, vol. 3, pp. 217-219 (1955).
Supplementary European Search Report Dated Feb. 16, 2006.
International Search Report (Apr. 14, 2003).

*Primary Examiner*—Elli Peselev
(74) *Attorney, Agent, or Firm*—Rader, Fishman & Grauer, PLLC

(57) ABSTRACT

A process for producing a 1,2-diol through the reaction of an olefin with hydrogen peroxide. The process is highly efficient and highly selective and catalyst recovery and reuse are easy. It does not use any strong acid or strong base causative of apparatus corrosion. The process for producing a 1,2-diol is characterized by reacting an olefin with hydrogen peroxide in the presence of a polymer having a sulfo group.

5 Claims, No Drawings

PROCESS FOR PRODUCING 1,2-DIOL

CROSS-REFERENCE TO RELATED APPLICATIONS

This is a national stage of application No. PCT/JP03/00593, filed Jan. 23, 2003.

TECHNICAL FIELD

The present invention relates to a novel method for producing a 1,2-diol compound by a reaction between an olefin compound and hydrogen peroxide. The 1,2-diol compound produced by the method of the invention is a useful compound that can be used widely in various industrial fields including chemical industry such as lubricants, cosmetics, perfumes, materials for pharmaceuticals, etc.

BACKGROUND ART

Methods of producing a 1,2-diol by reacting an olefin with an aqueous hydrogen peroxide solution in formic acid or acetic acid to synthesize an epoxide and then by hydrolyzing the epoxide have been known for a long time (*Organic Syntheses, Coll.* Vol. 3, 217-219 (1955), *J. Am. Chem. Soc.*, 67, 1786-1788 (1945), etc.) The methods require multi-step operations after the reactions, such as removing the solvent, reacting with an aqueous sodium hydroxide solution, and neutralizing with hydrochloric acid.

Another method of producing a 1,2-diol from an olefin via an epoxide by using peracetic acid as an oxidizing agent has been known (JP-A-4-41449). However, the method has problems such as corrosion of a reaction vessel, treatment of by-product acetic acid, etc.

In view of overcoming the problems by using an appropriate catalyst, methods of producing a 1,2-diol from an aqueous hydrogen peroxide and an olefin in one step using a tungsten complex catalyst have been reported (*J. Chem. Soc.*, 1949, 2988-3000, *J. Am. Oil Chem. Soc.*, 44, 316-320 (1967), *Tetrahedron Lett.*, 29, 823-826 (1988), etc.) However, since the diol thus produced can be further oxidized, a ketone or a carboxylic acid is inevitably generated as a by-product.

Though attempts have been made to improve the 1,2-diol selectivity by tuning the reaction conditions (EP 146374; *Synthesis*, 1989, 295-297, etc.), the methods use highly-toxic benzene as a solvent and require complicated operations for isolating the product such as extraction using a 30% aqueous sulfuric acid solution and neutralization using a base.

Reactions between an olefin and an aqueous hydrogen peroxide using a solid catalyst such as TS-1 and MCM-41, which can be easily removed by filtration and reused, have recently been reported (*J. Cat.*, 145, 151-158 (1994); *Chem. Commun.*, 1998, 325-326; *J. Cat.*, 189, 40-51 (2000), etc.) Though these reactions provide improved methods with respect to the operations, the reactions form a large amount of an epoxide or a ketone in addition to the desired 1,2-diol product, resulting in poor yield and low selectivity of the 1,2-diol. Thus, the development of a method capable of producing a 1,2-diol with high efficiency and high selectivity by a simple operation, using a catalyst that is easily recovered and reused without using a strong acid and a strong base causing the corrosion of a reaction vessel, has been strongly demanded.

DISCLOSURE OF THE INVENTION

An object of the present invention is to provide a method for producing a 1,2-diol compound by a reaction between an olefin compound and hydrogen peroxide with high efficiency and high selectivity, in which a catalyst can be easily recovered and reused, and in which a strong acid or a strong base causing the corrosion of a reaction vessel is not used.

As a result of intense research in view of the above object, the inventors have found that a 1,2-diol compound can be produced with high efficiency and high selectivity by reacting an olefin compound with hydrogen peroxide in the presence of a polymer compound having a sulfonic acid group, which can be easily recovered and reused. The present invention has been accomplished by this finding.

Thus, the invention relates to a method for producing a 1,2-diol compound represented by the general formula [2]:

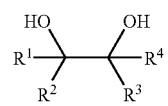

[2]

wherein $R^1$, $R^2$, $R^3$, and $R^4$ independently represent a hydrogen atom, a carboxyl group, a cyano group, a nitro group, a sulfonic acid group, an alkyl group which may have a substituent, a cycloalkyl group which may have a substituent, an aryl group which may have a substituent, an aralkyl group which may have a substituent, a heterocyclic group which may have a substituent, an alkoxy group which may have a substituent, an alkoxycarbonyl group which may have a substituent, an acyl group which may have a substituent, an amide group which may have a substituent, a silyl group which may have a substituent, a phosphoryl group which may have a substituent, a sulfinyl group which may have a substituent, a sulfonyl group which may have a substituent, or a sulfonate group which may have a substituent. Any two of $R^1$, $R^2$, $R^3$, and $R^4$ may lose a hydrogen atom to be bonded together to form a ring with a carbon atom bonding to them, and any two of $R^1$, $R^2$, $R^3$, and $R^4$ may lose a hydrogen atom and be bonded through a divalent atom and/or a divalent functional group to form a ring with a carbon atom bonding to them, characterized by reacting an olefin compound represented by the general formula [1]:

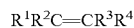

[1]

wherein $R^1$, $R^2$, $R^3$, and $R^4$ are as defined above, with hydrogen peroxide in the presence of a polymer compound having a sulfonic acid group.

BEST MODE FOR CARRYING OUT THE INVENTION

In the general formula [1], in the case where $R^1$, $R^2$, $R^3$, or $R^4$ is an alkyl group that may have a substituent, the alkyl group may be a straight or branched alkyl group having 1 to 30 carbon atoms, preferably 1 to 20 carbon atoms, and specific examples thereof include a methyl group, an ethyl group, a propyl group, a hexyl group, an octyl group, etc. In the case where $R^1$, $R^2$, $R^3$, or $R^4$ is a cycloalkyl group that may have a substituent, the cycloalkyl group may be a monocyclic, polycyclic, or condensed cycloalkyl group having 3 to 20 carbon atoms, preferably 3 to 10 carbon atoms, and specific examples thereof include a cyclopropyl group, a cyclopentyl group, a cyclohexyl group, a cyclooctyl group, etc. In the case where $R^1$, $R^2$, $R^3$, or $R^4$ is an aryl group that may have a substituent, the aryl group may be a monocyclic, polycyclic, or condensed, aromatic hydrocarbon group having 6 to 20 carbon atoms, preferably 6 to 14 carbon atoms, and specific examples thereof include a phenyl group, a tolyl group, xylyl group, a naphthyl group, a methylnaphthyl group, an anthryl group, a phenanthryl group, a biphenyl group, etc. In the case where $R^1$, $R^2$, $R^3$, or $R^4$ is an aralkyl group that may have a substituent, the aralkyl group may be a monocyclic, polycyclic, or condensed aralkyl group having 7 to 20 carbon atoms, preferably 7 to 15 carbon atoms, and specific examples thereof include a benzyl group, a phenethyl group, a naphthylmethyl group, a naphthylethyl group, etc. In the case where $R^1$, $R^2$, $R^3$, or $R^4$ is a heterocyclic group that may have a substituent, the heterocyclic group may be a monocyclic, polycyclic, or condensed, being saturated or unsaturated, heterocyclic group, which contains at least one nitrogen, oxygen, or sulfur atom in the ring, having a 3- to 15-membered ring structure, preferably a 3- to 10-membered ring structure, and may be condensed with a carbocyclic ring group such as a cycloalkyl group, a cycloalkenyl group, and an aryl group. Specific examples thereof include an oxiranyl group, a pyridyl group, a thienyl group, a phenylthienyl group, a thiazolyl group, a furyl group, a piperidyl group, a piperazyl group, a pyrrolyl group, an imidazolyl group, a quinolyl group, a pyrimidyl group, etc.

In the case where $R^1$, $R^2$, $R^3$, or $R^4$ is an alkoxy group that may have a substituent, the alkoxy group may be a straight or branched alkoxy group having 1 to 20 carbon atoms, preferably 1 to 10 carbon atoms, and specific examples thereof include a methoxy group, an ethoxy group, an i-propoxy group, a t-butoxy group, etc. In the case where $R^1$, $R^2$, $R^3$, or $R^4$ is an alkoxycarbonyl group that may have a substituent, the alkoxycarbonyl group may be a straight or branched alkoxycarbonyl group having 2 to 31 carbon atoms, preferably 2 to 21 carbon atoms, and specific examples thereof include a methoxycarbonyl group, an ethoxycarbonyl group, an i-propoxycarbonyl group, a t-butoxycarbonyl group, a phenoxycarbonyl group, etc. In the case where $R^1$, $R^2$, $R^3$, or $R^4$ is an acyl group that may have a substituent, the acyl group may be a straight or branched acyl group having 2 to 31 carbon atoms, preferably 2 to 21 carbon atoms, and specific examples thereof include an acetyl group, a benzoyl group, a heptanoyl group, a cyclohexanecarbonyl group, etc. In the case where $R^1$, $R^2$, $R^3$, or $R^4$ is an amide group that may have a substituent, the substituted amide group may be a straight or branched, having 2 to 31 carbon atoms, preferably 2 to 21 carbon atoms, and specific examples thereof include a methylamide group, an ethylamide group, an i-propylamide group, a tetradecylamide group, etc. In the case where $R^1$, $R^2$, $R^3$, or $R^4$ is a silyl group that may have a substituent, specific examples of the substituted silyl groups include a trimethylsilyl group, a triethylsilyl group, a triphenylsilyl group, etc. In the case where $R^1$, $R^2$, $R^3$, or $R^4$ is a phosphoryl group that may have a substituent, specific examples of the substituted phosphoryl groups include a dihydroxyphosphoryl group, a dimethoxyphosphoryl group, etc. In the case where $R^1$, $R^2$, $R^3$, or $R^4$ is a sulfinyl group that may have a substituent, specific examples of the substituted sulfinyl groups include a methylsulfinyl group, a phenylsulfinyl group, etc. In the case where $R^1$, $R^2$, $R^3$, or $R^4$ is a sulfonyl group that may have a substituent, specific examples of the substituted sulfonyl groups include a methylsulfonyl group, a phenylsulfonyl group, etc. In the case where $R^1$, $R^2$, $R^3$, or $R^4$ is a sulfonate group that may have a substituent, specific examples of the substituted sulfonate groups include a methylsulfonate group, a phenylsulfonate group, etc.

The above alkyl group, the cycloalkyl group, the aryl group, the aralkyl group, the heterocyclic group, the alkoxy group, the alkoxycarbonyl group, the acyl group, the amide group, the silyl group, the phosphoryl group, the sulfinyl group, the sulfonyl group, and the sulfonate group may have any substituent that has no adverse affects on the reaction. Examples of the substituents include alkyl groups such as a methyl group, an ethyl group, and a propyl group; aryl groups such as a phenyl group and a naphthyl group; heterocyclic groups such as an oxiranyl group, a pyridyl group, and a furyl group; alkoxy groups such as a methoxy group, an ethoxy group, a phenoxy group, and a naphthyloxy group; alkoxycarbonyl groups such as a methoxycarbonyl group, an i-propoxycarbonyl group, a t-butoxycarbonyl group, and a phenoxycarbonyl group; a sulfonic acid group; a cyano group; a nitro group; silyl groups such as a trimethylsilyl group and a triphenylsilyl group; a hydroxy group; amide groups such as an unsubstituted amide group, a methylamide group, a propylamide group, and a tetradecylamide group; acyl groups such as an acetyl group and a benzoyl group; phosphoryl groups such as a dihydroxyphosphoryl group and a dimethoxyphosphoryl group; sulfinyl groups such as a methylsulfinyl group and a phenylsulfinyl group; sulfonyl groups such as a methylsulfonyl group and a phenylsulfonyl group; sulfonate groups such as a methylsulfonate group and a phenylsulfonate group; etc.

In the case where any two of $R^1$, $R^2$, $R^3$, and $R^4$ lose a hydrogen atom respectively and the residues are bonded together to form a ring with a carbon atom bonding to them, the ring may be a cycloalkane ring, a cycloalkene ring, a cycloalkadiene ring, etc., and specific examples of the rings include a cyclopropane ring, a cyclopentane ring, a cyclohexane ring, a cyclooctane ring, a cyclopentene ring, a cyclohexene ring, a cyclooctene ring, a cyclopentadiene ring, a cyclohexadiene ring, a cyclooctadiene ring, etc. These rings may form a polycyclic ring such as a condensed ring and an uncondensed ring with another ring.

Furhter, in the case where any two of $R^1$, $R^2$, $R^3$, and $R^4$ lose a hydrogen atom respectively and the residues are bonded through a divalent atom and/or a divalent functional group to form a ring with a carbon atom bonding to them, examples of the divalent atoms include an oxygen atom, a nitrogen atom, a sulfur atom, etc., and examples of the divalent functional groups include silylene groups, an ethylenedioxy group, arylenedioxy groups, a carbonyl group, a sulfoxide group, a sulfone group, etc.

Specific examples of the olefin compounds represented by the general formula [1] used in the method of the present invention include 2,3-dimethyl-2-butene, 2-methyl-2-pentene, 2-heptene, cyclopentene, cyclohexene, 1-methylcyclohexene, cyclooctene, cyclododecene, 1,4-cyclohexadiene, allyl alcohol, oleic acid, etc.

In the method of the invention, hydrogen peroxide is generally used in the form of an aqueous solution. The concentration of the aqueous solution is not restricted, and the reaction of the olefin proceeds depending on the concentration. The concentration is generally 1 to 80%, preferably 3 to 60%.

The amount of the aqueous hydrogen peroxide solution is not restricted, and the reaction of the olefin proceeds depending on the amount. The amount is generally 1.0 to 20.0 equivalents, preferably 1.0 to 5.0 equivalents, per double bond moiety of the olefin compound.

In the method of the invention, the reaction is generally carried out at 30 to 120° C. Though the reaction can proceed without solvents, the reaction may be carried out in a solvent such as an alcohol, an ether, an ester, a nitrile, an amide, a sulfoxide, a hydrocarbon, or a mixture thereof, etc. The amount of the solvent is not restricted, and is generally 0.5 to 10 volume equivalents, preferably 1.0 to 3.0 volume equivalents, relative to the volume of the olefin compound. Examples of the solvents preferred in the reaction of the invention include methanol, t-butyl alcohol, 1,4-dioxane, THF, acetonitrile, toluene, etc.

The method of the invention is characterized by that the reaction is carried out in the presence of the polymer compound having a sulfonic acid group, which remarkably accelerates the reaction. The polymer compound having a sulfonic acid group with any polymeric structure can act as a catalyst. The polymer compound preferably has a side chain comprising a sulfonic acid group, and it is preferable that the solvent used in the reaction does not dissolve the polymer compound, from the viewpoint of recovering the catalyst. In general, styrene polymers, styrene-divinylbenzene copolymers, and fluorocarbon resins, which have a side chain comprising a sulfonic acid group, are industrially easily available. Commercially-available polymer compounds include styrene polymers such as Amberlyst 15 available from Organo Corporation and Daiaion PK228 available from Mitsubishi Chemical Corporation, styrene-divinylbenzene copolymers such as MSC-1 available from Muromachi Technos Co., Ltd., and fluorocarbon resins such as Nafion-NR50 and Nafion-SAC13 available from Du Pont, which can be preferably used in the reaction of the invention.

The reaction proceeds at a higher rate as the amount of the polymer compound having a sulfonic acid group becomes larger, whereby the equivalent ratio between the olefin compound and the sulfonic acid group may be such that the sulfonic acid group is used in large excess. However, although depending on the reaction temperature, even if the amount of the sulfonic acid group is 1 equivalent or less per the olefin compound, it is possible to achieve a high yield in a relatively short time. The amount of the sulfonic acid group is generally 0.00001 to 10 equivalents, preferably 0.001 to 1 equivalents, per olefin compound.

The polymer compound having a sulfonic acid group used in the reaction can be easily separated from the reaction mixture by a common separation procedure such as filtration and decantation, and the recovered polymer compound can be repeatedly used as it is.

The present disclosure relates to subject matter contained in Japanese Patent Application No. 2002-015146 which is expressly incorporated herein by reference in its entirety.

EXAMPLES

The present invention will be explained below in more detail referring to Examples without intention of restricting the invention.

Example 1

Nafion-NR50 available from Du Pont (500 mg, the amount of the sulfonic acid groups is 0.04 equivalents per olefin compound), a 30% aqueous hydrogen peroxide solution (2.23 g, 19.6 mmol), and cyclohexene (810 mg, 9.81 mmol) were mixed and stirred at 70° C. for 20 hours. After the reaction, Nafion-NR50 was removed from the reaction mixture by filtration, and manganese dioxide (10 mg, 0.115 mmol) was added to the filtrate to decompose the excess hydrogen peroxide. The resultant mixture was filtered, and water, etc. in the mixture was distilled off by a rotary evaporator, to obtain 1.12 g (9.63 mmol) of white powder of trans-1,2-cyclohexanediol (97.7% yield). The obtained white powder was recrystallized from acetone to obtain white crystals of trans-1,2-cyclohexanediol with a yield of 82.0%.

Comparative Example 1

A 30% aqueous hydrogen peroxide solution (2.23 g, 19.6 mmol) and cyclohexene (810 mg, 9.81 mmol) were mixed and stirred at 70° C. for 20 hours. The resultant mixture was treated in the same manner as Example 1 to obtain 11.4 mg (0.098 mmol) of white powder of trans-1,2-cyclohexanediol (1.0% yield).

Example 2

Nafion-NR50 recovered from the reaction of Example 1 by filtration was washed with a small amount of water, and reused in the reaction between cyclohexene (9.81 mmol) and a 30% aqueous hydrogen peroxide solution (19.6 mmol). The reaction was carried out at 70° C. for 20 hours to obtain trans-1,2-cyclohexanediol with a yield of 95.9%. Nafion-NR50 was further reused repeatedly 10 times in the same manner, and each of the 10 reactions afforded trans-1,2-cyclohexanediol with an isolated yield of 94% or more. The results are shown in Table 1.

TABLE 1

| | Repeated run number using recovered Nafion catalyst | | | | | | | | |
|---|---|---|---|---|---|---|---|---|---|
| | 2 | 3 | 4 | 5 | 6 | 7 | 8 | 9 | 10 |
| Isolated yield (%) | 95.9 | 96.2 | 96.7 | 96.0 | 94.3 | 94.0 | 95.5 | 95.0 | 96.1 |

Examples 3 and 4

Cyclohexene (9.81 mmol) and a 30% aqueous hydrogen peroxide solution (19.6 mmol) were reacted at 70° C. for 20 hours in the same manner as Example 1 except for changing the amount of Nafion-NR50. The yields of trans-1,2-cyclohexanediol obtained under each reaction condition are shown in Table 2.

TABLE 2

| Example | Amount of Nafion (mg) | Isolated yield (%) |
|---|---|---|
| 3 | 115 | 11.6 |
| 4 | 294 | 64.9 |

Examples 5 to 7

Cyclohexene (9.81 mmol) and a 30% aqueous hydrogen peroxide solution (19.6 mmol) were reacted at 70° C. in the presence of Nafion-NR50 (500 mg) in the same manner as Example 1. The yields of trans-1,2-cyclohexanediol obtained in different reaction times are shown in Table 3.

TABLE 3

| Example | Reaction time (h) | Isolated yield (%) |
|---|---|---|
| 5 | 2 | 5.6 |
| 6 | 5 | 12.6 |
| 7 | 10 | 41.4 |

Examples 8 to 10

Cyclohexene (9.81 mmol) and a 30% aqueous hydrogen peroxide solution 19.6 mmol) were reacted at 70° C. for 20 hours using various polymers having a sulfonic acid group. The yields of trans-1,2-cyclohexanediol are shown in Table 4.

TABLE 4

| Example | Polymer with sulfonic acid group | Amount of polymer (mg) | Isolated yield (%) |
|---|---|---|---|
| 8 | Nafion-SAC13 | 509 | 94.9 |
| 9 | Amberlyst 15 | 507 | 82.8 |
| 10 | Daiaion PK228 | 499 | 22.3 |

Examples 11 to 16

Cyclohexene (9.81 mmol) and a 30% aqueous hydrogen peroxide solution 19.6 mmol) were reacted at 70° C. for 5 hours in the presence of Nafion-NR50 (500 mg) using various solvents (1 volume equivalent per olefin compound). The yields of trans-1,2-cyclohexanediol are shown in Table 5.

TABLE 5

| Example | Solvent | Isolated yield (%) |
|---|---|---|
| 11 | 1,4-Dioxane | 30.9 |
| 12 | Acetonitrile | 27.3 |
| 13 | Methanol | 21.6 |
| 14 | t-Butyl alcohol | 15.9 |
| 15 | THF | 14.8 |
| 16 | Toluene | 6.3 |

Example 17

Nafion-NR50 (500 mg), a 30% aqueous hydrogen peroxide solution (2.0 mL, 20.3 mmol), and 2,3-dimethyl-2-butene (1.17 mL, 9.87 mmol) were mixed and stirred at 70° C. for 20 hours. Quantitative analysis by $^1$H-NMR revealed that the yield of 2,3-dimethyl-2,3-butanediol was 85.9%.

Example 18

Nafion-NR50 (495 mg), a 30% aqueous hydrogen peroxide solution (2.0 mL, 20.3 mmol), 2-methyl-2-pentene (1.08 mL, 8.85 mmol) were mixed and stirred at 70° C. fir 20 hours. Quantitative analysis by $^1$H-NMR revealed that the yield of 2-methyl-2,3-pentanediol was 83.0%.

Example 19

Nafion-NR50 (499 mg), a 30% aqueous hydrogen peroxide solution (2.0 mL, 20.3 mmol), and trans-2-heptene (1.24 mL, 8.84 mmol) were mixed and stirred at 70° C. for 20 hours. Quantitative analysis by $^1$H-NMR revealed that the yield of 2,3-heptanediol was 66.0%.

Example 20

Nafion-NR50 (500 mg), a 30% aqueous hydrogen peroxide solution (2.0 mL, 20.3 mmol), and cyclopentene (0.88 mL, 10.0 mmol) were mixed and stirred at 40° C. for 20 hours. Quantitative analysis by $^1$H-NMR revealed that the yield of trans-1,2-cyclopentanediol was 80.3%.

Example 21

Nafion-NR50 (502 mg), a 30% aqueous hydrogen peroxide solution (2.0 mL, 20.3 mmol), and 1-methylcyclohexene (1.17 mL, 9.85 mmol) were mixed and stirred at 70° C. for 20 hours. After the reaction, the resultant mixture was treated in the same manner as Example 1 to obtain 1.10 g (8.43 mmol) of 1-methyl-1,2-cyclohexanediol (85.6% yield).

Example 22

Nafion-NR50 (501 mg), a 30% aqueous hydrogen peroxide solution (2.0 mL, 20.3 mmol), and 1,4-cyclohexadiene (0.92 mL, 9.86 mmol) were mixed and stirred at 70° C. for 20 hours. Quantitative analysis by $^1$H-NMR revealed that the yield of 1,2,4,5-cyclohexanetetraol was 92.3%.

Example 23

Nafion-NR50 (507 mg), a 30% aqueous hydrogen peroxide solution (2.0 mL, 20.3 mmol), and allyl alcohol (0.68 mL, 9.90 mmol) were mixed and stirred at 70° C. for 20 hours. After the reaction, the resultant mixture was treated in the same manner as Example 1 to obtain 912 mg (9.90 mmol) of glycerol (100% yield).

Example 24

Nafion-SAC13 (1.50 g), a 30% aqueous hydrogen peroxide solution (4.0 mL, 40.6 mmol), and oleic acid (3.20 mL, 10.1 mmol) were mixed and stirred at 90° C. for 20 hours. After the reaction, the resultant mixture was treated in the same manner as Example 1 to obtain 2.57 g (8.11 mmol) of 9,10-dihydroxyoctadecanoic acid (80.3% yield).

INDUSTRIAL APPLICABILITY

In the method of the present invention, a useful 1,2-diol compound, which has been widely used for lubricants, cosmetics, perfumes, materials for pharmaceuticals, etc., can be efficiently and safely produced by the reaction between a corresponding olefin compound and hydrogen peroxide. The polymer compound having a sulfonic acid group used in the reaction can be separated from the reaction system and reused easily. Thus, the invention has large industrial advantageous effects.

The invention claimed is:

1. A method for producing a 1,2-diol compound represented by the general formula [2]:

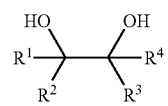

[2]

wherein $R^1$, $R^2$, $R^3$, and $R^4$ independently represent a hydrogen atom or an alkyl group having 1-30 carbons in a straight or branched chain with or without a substituent selected from an alkoxy group, an alkoxycarbonyl group, a sulfonic acid group, a cyano group, a nitro group, a hydroxyl group, or a carboxyl group, or wherein any two of $R^1$, $R^2$, $R^3$, and $R^4$ lose a hydrogen atom to be bonded together to form a cycloalkane ring with a carbon atom bonding to any two of $R^1$, $R^2$, $R^3$, and $R^4$, comprising reacting an olefin compound represented by the general formula [1]:

$$R^1R^2C=CR^3R^4 \quad [1]$$

wherein $R^1$, $R^2$, $R^3$, and $R^4$ are as defined above, with hydrogen peroxide in the presence of a polymer compound having a sulfonic acid group (with the proviso that a silicon oxide-titanium oxide based synthetic zeolite is not used as a catalyst in combination with the polymer compound).

2. The method according to claim 1, wherein the hydrogen peroxide is in the form of an aqueous hydrogen peroxide solution.

3. The method according to claim 1 or 2, wherein the polymer compound having a sulfonic acid group is a styrene polymer having a sulfonic acid group in a side chain of the polymer.

4. The method according to claim 1 or 2, wherein the polymer compound having a sulfonic acid group is a styrene-divinylbenzene copolymer having a sulfonic acid group in a side chain of the polymer.

5. The method according to claim 1 or 2, wherein the polymer compound having a sulfonic acid group is a fluorocarbon resin having a sulfonic acid group in a side chain of the polymer.

* * * * *